United States Patent [19]

Richardson et al.

[11] Patent Number: 5,145,637
[45] Date of Patent: Sep. 8, 1992

[54] INCORE HOUSING EXAMINATION SYSTEM

[75] Inventors: David L. Richardson, Los Gatos; David C. Berg; Balasubramanian S. Kowdley, both of San Jose; Jack T. Matsumoto, Sunnyvale; Thurman D. Smith; Jack P. Clark, both of San Jose, all of Calif.

[73] Assignee: General Electric Company, San Jose, Calif.

[21] Appl. No.: 747,404

[22] Filed: Aug. 19, 1991

Related U.S. Application Data

[63] Continuation of Ser. No. 527,927, May 24, 1990, abandoned.

[51] Int. Cl.$^5$ .......................................... G21C 17/003
[52] U.S. Cl. .................................... 376/249; 376/245; 376/252; 73/623
[58] Field of Search ............... 376/245, 252, 249, 263; 73/623

[56] References Cited

U.S. PATENT DOCUMENTS

| | | | |
|---|---|---|---|
| 3,664,922 | 5/1972 | Diwinsky et al. | 176/19 R |
| 3,926,040 | 12/1975 | Cowell | 73/67.85 |
| 4,037,465 | 7/1977 | Cook et al. | 73/67.85 |
| 4,506,549 | 3/1985 | Thome | 73/582 |
| 4,642,215 | 2/1987 | Klinvex et al. | 376/249 |
| 4,665,734 | 5/1987 | Joet | 73/622 |
| 4,826,650 | 5/1989 | Richardson et al. | 376/249 |
| 4,856,337 | 8/1989 | Metala et al. | 73/601 |

FOREIGN PATENT DOCUMENTS 2-091598  3/1990  Japan .................. 376/245

Primary Examiner—Brooks H. Hunt
Assistant Examiner—Chrisman D. Carroll
Attorney, Agent, or Firm—Robert R. Schroeder

[57] ABSTRACT

An automated system for examining incore housing welds in a nuclear reactor from above is disclosed. The probe uses both ultrasonic and eddy current nondestructive inspection coils to examine the weld for indications, or flaws. It is inserted into the incore housing tube from above because of the high radiation exposure workers experienced using the prior method of inserting a probe into the incore housing from below. This is conveniently done when the incore flux monitors are removed during standard maintenance, and is performed from the refueling bridge.

16 Claims, 10 Drawing Sheets

INCORE HOUSING EXAMINATION SYSTEM

This is a continuation of copending U.S. patent application Ser. No. 07/527,927, filed May 24, 1990, now abandoned.

BACKGROUND OF THE INVENTION

This invention relates to the non-destructive examination of welds and tubes inside a nuclear reactor pressure vessel. In particular, this invention relates to the examination of the welds attaching the incore housing to the reactor pressure vessel using ultrasonic transducers. This invention also relates to the eddy current surface examination of the incore housing tubes.

In a conventional boiling water reactor, the reactor core comprises a plurality of fuel assemblies arranged in a spaced array and oriented vertically. Each fuel assembly consists of a fuel bundle and its carrying case, called a fuel channel. Fuel assemblies are grouped in sets of four with a control rod interposed between the four assemblies in each set. The control rods contain a neutron absorbing material, and are inserted between the fuel assemblies in varying degrees to control the reactivity of the core. The entire core is immersed in water which serves as a coolant, as well as a neutron moderator. All these are contained in the reactor pressure vessel.

Interdispersed throughout the core between the fuel assemblies are removable dry-tubes, which house incore flux monitors and other instrumentation. Dry-tubes rest on the lower core support plate, and extend to the top guide, at the top of the core. Below the dry-tubes, and extending through the bottom head of the pressure vessel the guide and incore housing tube configurations are welded in place. The guide tubes extend downward from the lower core support plate to the tops of the incore housing tubes, which then extend through the pressure vessel. The bottoms of the guide tubes are welded to the tops of the incore housing tubes, forming a single unit. A reactor will have anywhere from twenty to sixty such tube configurations, depending on its size.

Nuclear reactors constitute extremely hostile environments for manual examination of any kind. First, nuclear reactors have inherently high levels of radioactivity and radioactive contamination. Secondly, most of the reactor pressure vessel internals are inaccessible for almost any kind of manual examination. A classic example of such inaccessibility is the weld attaching the incore housing to the bottom head of a reactor pressure vessel.

The incore housing consists of stainless steel tubes which penetrate the bottom head of the pressure vessel. Attachment welds seal the boundary between the inner surface of the pressure vessel and the incore housing, as well as provide structural support for the incore housing. Any defects in the attachment welds, e.g. cracks, jeopardize the integrity of the pressure system.

Non-destructive examination of the attachment welds is used to verify their integrity or to discover any incipient defects, so necessary repairs can be made before failure occurs. An ultrasonic probe for "seeing" into the weld and surrounding metal is suitable for such an examination. Ultrasonic probes send a beam of sound waves through a region, and flaws (called indications) cause reflections which are detected and analyzed.

Ultrasonic probes have been used in the past to examine welds inside the reactor pressure vessel. Such a probe is described in "Stub Tube Inspection Device", U.S. Pat. No. 4,548,785, issued Oct. 22, 1985. In this patent a scanning tool, i.e. a device for moving the probe around the region of interest, is placed on top of a stub tube, and the probe is moved vertically along the outside of the stub tube during the scan, then rotated and moved vertically again for another scan. This is done with two tranducers, one which "looks" up, and one which "looks" down. On a given vertical sweep the upwards-looking transducer is on during the upsweep, and the downwards-looking transducer is on during the downsweep. Mechanical switches, at the top and bottom of the sweep, switch the transducers' activation states. No attention is paid to the rotational orientation of the transducers with respect to the reactor. This limits information as to the nature of any flaws since the inspected region is not rotationally symmetric.

The nature of weld inspection inside a pressure vessel is such that every situation requires an inspection device specially suited to the particular circumstances involved. For instance, the probe apparatus described in U.S. Pat. No. 4,548,785 can not be used to inspect incore housing welds because the incore housings are not "stubs", but rather part of a continuous tube structure that extends from below the pressure vessel through the bottom, and up to the bottom of the reactor core support plate. This makes it impractical to use any sort of probe external to the tube. The prior method of inspecting these welds involved removing a flange at the bottom of each incore housing tube outside the pressure vessel, and manually inserting a probe up to the weld area. This necessitates violating the pressure boundary of the pressure vessel, and is extremely unsatisfactory because of the the high levels of radiation to which workers are exposed. Workers must wear a "bubble suit" with an external air supply for radiation protection when performing this type of examination. Also, this process is awkward, expensive, and time consuming. Thus it became necessary to develop a new technique for incore housing inspection.

SUMMARY OF THE INVENTION

In accordance with the present invention, the ultrasonic examination of the incore housing welds is performed with access from above the welds, when the incore instrumentation is being checked and replaced. Examination from above results in a 100:1 reduction in the radiation per person exposure level when compared with the prior method of examining the welds from below. In further accordance with the present invention it is also desirable to perform non-destructive examination of the interior surface and near surface of the incore housing tubes for dents, cracks, corrosion, and the like. Eddy current coils are suitable for this type of examination.

Before anything inside the pressure vessel can be accessed from above its top head is removed. The removal of associated fuel assemblies, incore instrumentation (flux monitors), and dry tubes is also required in the areas where incore access is desired. Advantageously, the welds are checked when the incore instrumentation is replaced since this must be done periodically, using established procedures. Handling of equipment is accomplished using a hoist on a refueling bridge.

The basic mechanical unit used to examine the welds consists of a probe and a scanning tool, for controlling probe movement. The probe is attached to the scanning tool via a hollow probe tube, which is assembled from shorter sections to facilitate handling.

The probe has six ultrasonic transducers, with a "straight-on" transducer above the other five. "Straight-on" refers to the direction of the beam towards the incore housing, i.e. it is perpendicular to the surface of the housing. All of the transducers are focused at the border between the incore housing and the weld, and the five that are grouped together are focused at the same point. The transducers pulse in sequential order, at a high enough frequency relative to the probe speed to enable the five transducers with the same focal point to examine the same region simultaneously.

Prior to immersion the angular orientation of the probe tube with respect to the scanning tool is set so the "straight-on" transducer will initially face the same direction in each housing tube, which is defined to be a reference direction (0°) of the pressure vessel. Also, since the weld is at the same level as the inside surface of the bottom head of the pressure vessel, and the distance from the top guide to the bottom head of the pressure vessel is known, the probe tube is adjusted with respect to the scanning tool so that when the scanning tool is level with the top guide the probe is at weld level. When in place the probe and probe tube fit into the incore housing to be inspected, and the scanning tool is clamped to the top guide.

After incore access is obtained, the probe, probe tube, and scanning tool unit is positioned above the weld to be inspected. They are lowered into the water, and the probe and probe tube are lowered through the incore guide tube into the incore housing tube until the probe is at the level of the weld inspection region. The scanning tool is then clamped to the top guide in a pre-determined angular position with respect to the pressure vessel. The straight-on transducer now points in the pressure vessel reference direction. The probe is then rotated so the transducers face the high side of the weld. The degree of rotation varies depending on the particular incore housing being inspected. This is the basic starting position for the examination of the specified weld and housing.

Once the probe is in its initial position inside the housing its movement is controlled automatically for the respective ultrasonic and eddy current examinations. The initial position for the ultrasonic scan is when the ultrasonic centerline (the focal point of the lower five transducers) is at least 40 millimeters (mm) above the high side of the weld. Similarly, the initial position for the eddy current examination is when the eddy current centerline is 40 mm or more above the high side of the weld. The region from at least 40 mm above the high side of the weld to 40 mm or more below the low side of the weld is inspected in both the ultrasonic and eddy current examinations. The probe travels vertically in one direction, and then rotates by a small amount, e.g. 5°, and then travels vertically in the other direction. This is repeated until the probe has rotated the full 360°. All data is processed electronically, and the status of the examined region is determined.

DESCRIPTION OF THE PREFERRED EMBODIMENTS

Figure 1:
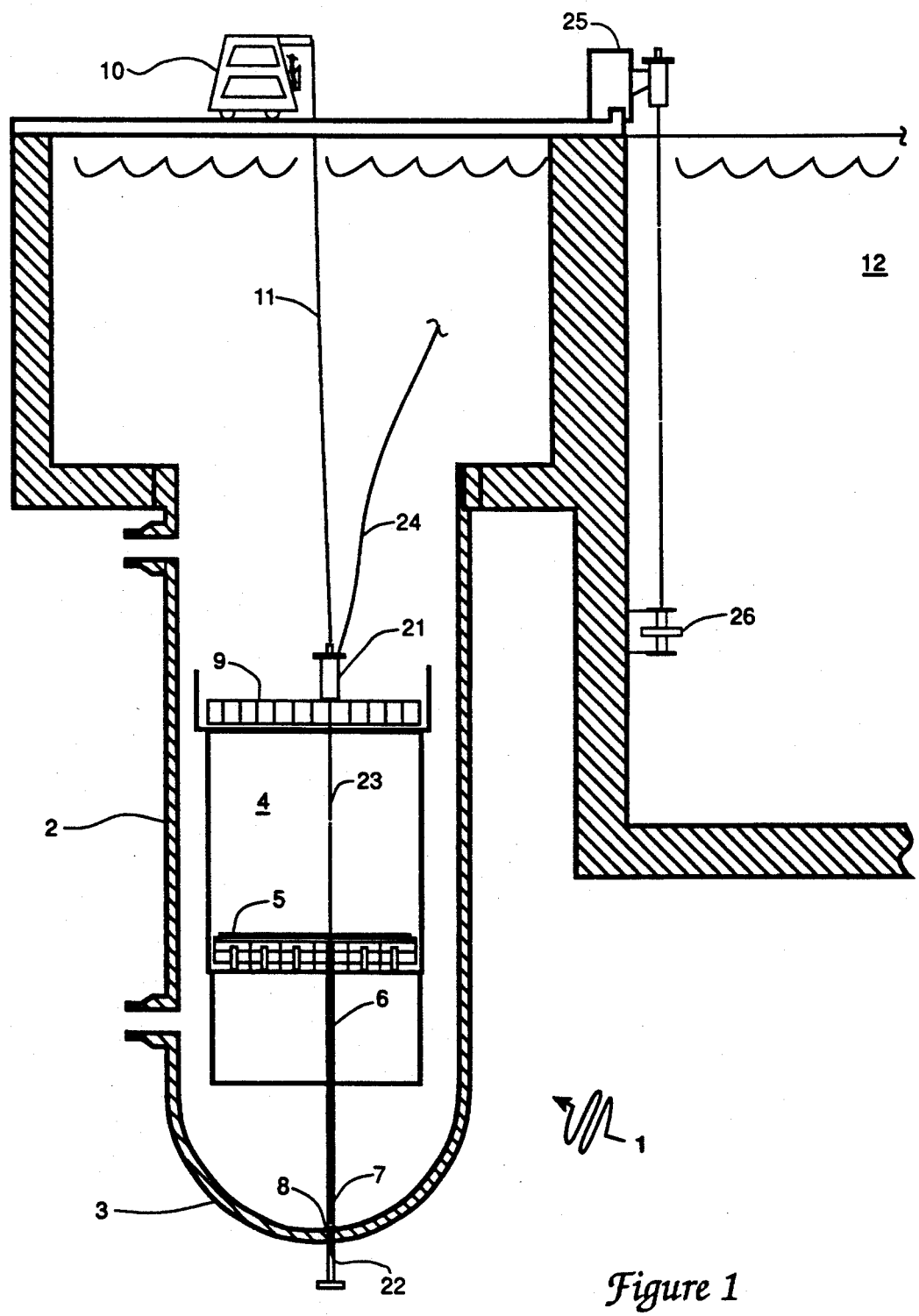
FIG. 1 is a schematic cross-sectional side view of a reactor showing the incore housing weld inspection equipment in place.

In accordance with the present invention, a boiling water reactor system 1 includes reactor pressure vessel 2 with bottom head 3, as shown in FIG. 1. Below reactor core 4 sits core support plate 5 with circular openings on which sit which fuel assemblies, dry-tubes, and other internal parts of the core. Dispersed below core 4 are incore guide tubes 6. These are welded to the top of incore housing tubes 7 that penetrate bottom head 3 of the pressure vessel wall. These penetrations are sealed with incore housing welds 8, which are crucial since the inside of pressure vessel 2 is under pressure and is radioactive. Access to this region, as well as core 4, is facilitated by top guide 9, which is a metal grid with a matrix of square openings. Equipment and parts in this region are handled from refueling bridge 10, which is a trolley that rides across the refueling platform on rails. A hoist on refueling bridge 10 uses hoist cable 11 to raise and lower equipment and parts into this region. Adjacent to pressure vessel 2 is a refueling pool 12, which contains spare reactor fuel.

In order to check the region around weld 8 for flaws a combination of ultrasonic testing of the weld region, and eddy current testing of the inner surface of housing tube 7 is employed. A submersible device for performing such an examination is shown in FIG. 1; hoist cable 11 is used to lower a unit including scanning tool 21, probe 22, and probe tube 23 into position at the weld to be tested. Probe 22 is lowered through incore guide tube 6 and incore housing tube 7 until it is level with weld 8, and scanning tool 21 is clamped to top guide 9 with a mechanical clamping device. Probe tube 23 is clamped to scanning tool 21 at a previously determined location so that when scanning tool 21 and top guide 9 are at the same level, probe 22 and weld 8 are at the same level.

Scanning tool 21 moves probe 22 automatically to perform the inspection, and data is sent to electronic processing and control equipment outside pressure vessel 2 via cable bundle 24 for analysis. Wiring to probe 22 runs through probe tube 23. The nature of any defects found during inspection is determined with reference to a previously manufactured set of defects found in calibration standard 26, which is a duplication of the housing weld configuration. Support bracket 25 is used for storage as well as calibration of the inspection equipment.

Figure 2:
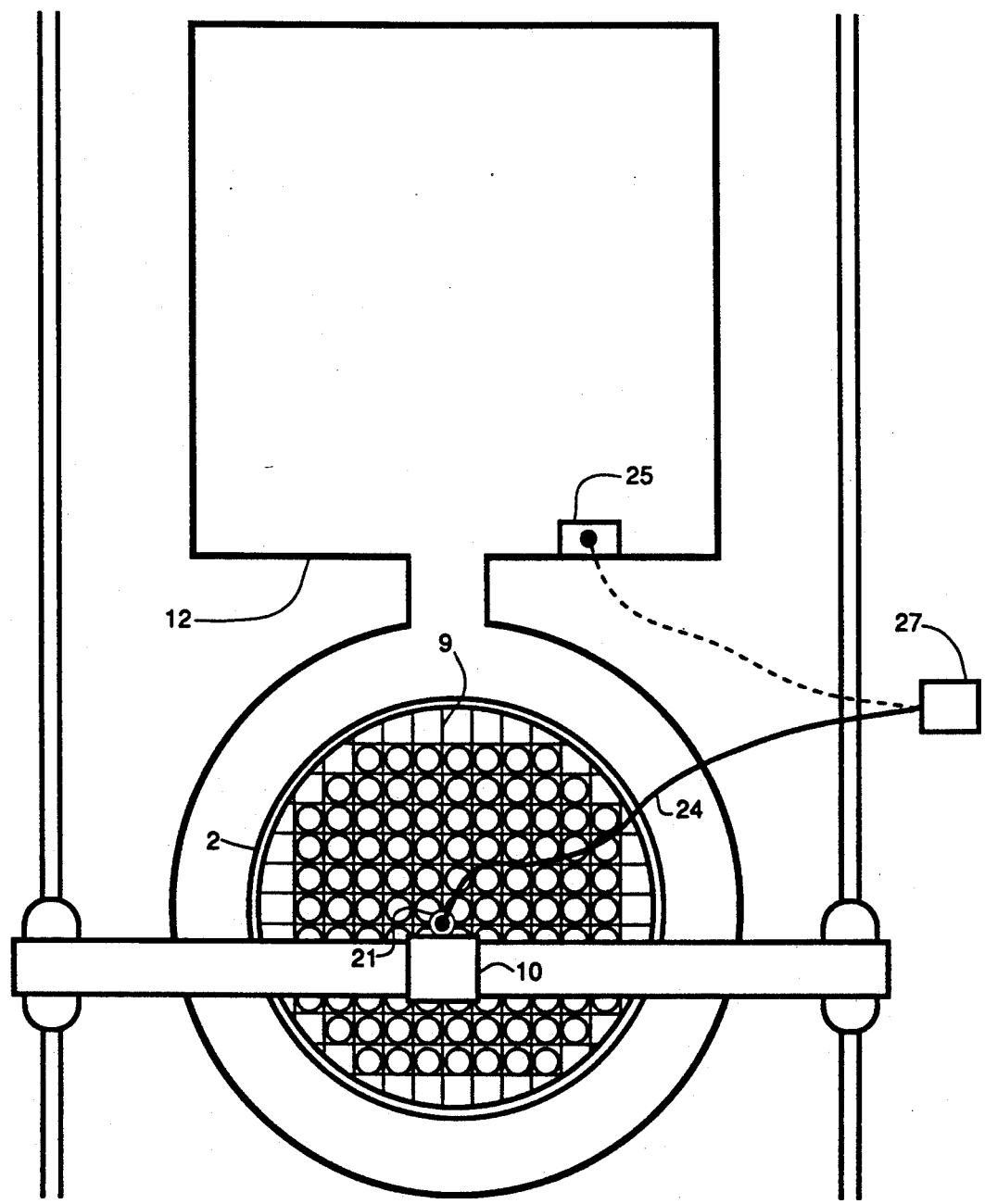
FIG. 2 is a schematic plan view of a reactor showing the incore housing weld inspection equipment in place.

Positioning of the incore housing inspection equipment is most easily seen from above the reactor, as shown in FIG. 2. The inspection equipment is moved using refueling bridge 10 until scanning tool 21 is located above an incore housing. These are below the intersections in the metal matrix of top guide 9. Scanning tool 21 is mounted at such an intersection for weld inspection. The hoist on refueling bridge 10 moves equipment in the vertical direction. Bridge 10 moves along the refueling platform on rails, which in turn moves between pressure vessel 2 and refueling pool 12, also along two parallel rails. Cable bundle 24 sends commands to scanning tool 21 and the probe (beneath the scanning tool), as well as carries data back to work station 27, which is outside the pressure vessel.

Figure 3:
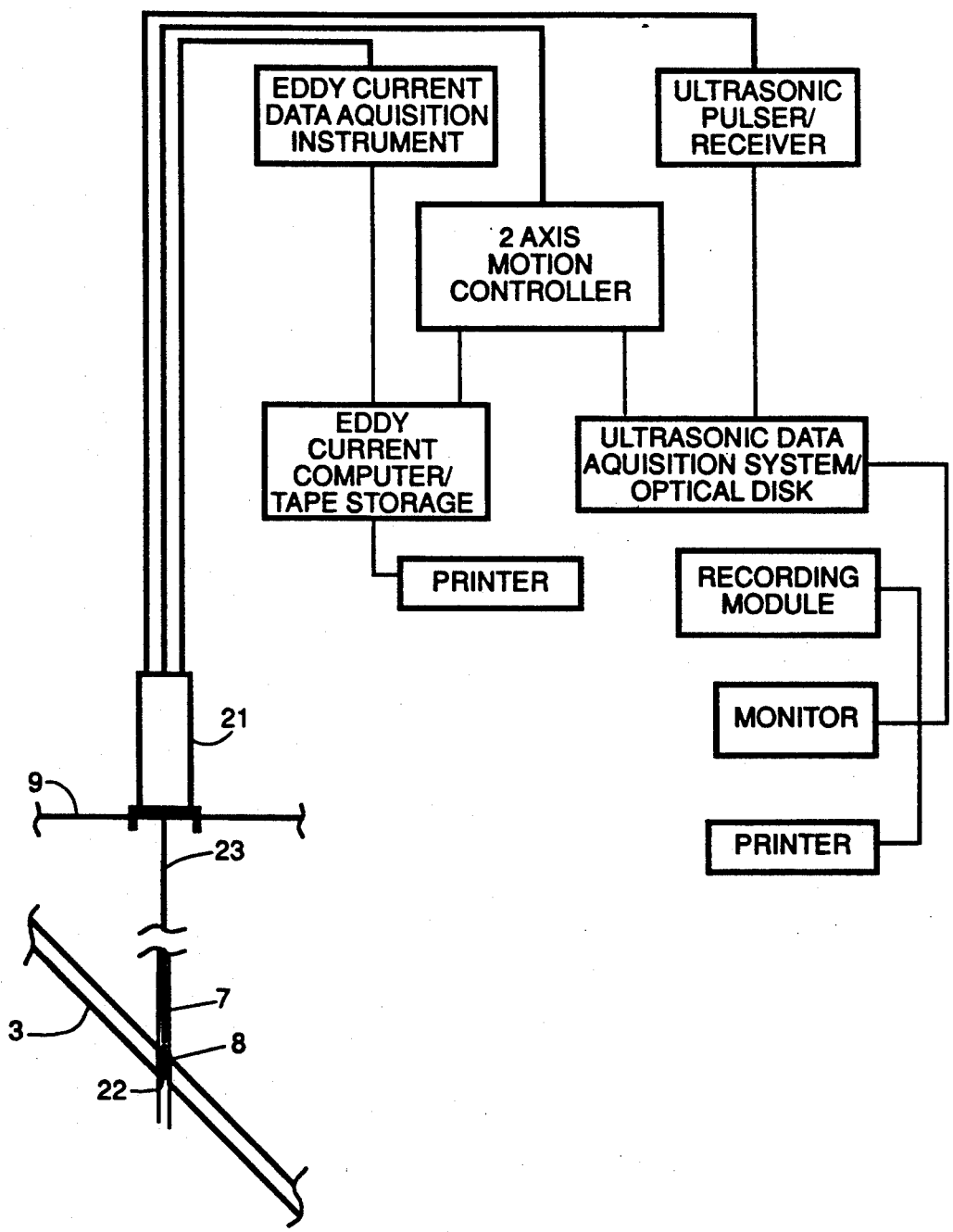
FIG. 3 is a schematic view of the incore housing weld inspection equipment including electronic components.

FIG. 3 shows a side view of the inspection equipment, and also shows a box diagram of the electronic gear used to control and receive data from the inspection equipment. Relative electrical impedance data (both vertical and horizontal components) is digitally recorded for the four eddy current coils with the eddy current instrument, eddy current computer, and storage tape. The eddy current instrument records raw data, and the eddy current computer prepares it for storage. The eddy current instrument also drives the eddy current coils, and can drive each one independently at different frequencies. Reflection data for the six ultrasonic transducers is recorded with a pulser/receiver, data aquisition unit (which includes a central processing unit), and an optical disk recording module. Both systems are connected to the motion controller, which is connected to the motors and position encoders in scanning tool 21 to move probe 22 automatically. Both systems also have printers for hard copy read-outs. The ultrasonic system also has a monitor for an electronic read-out.

Figure 4A:
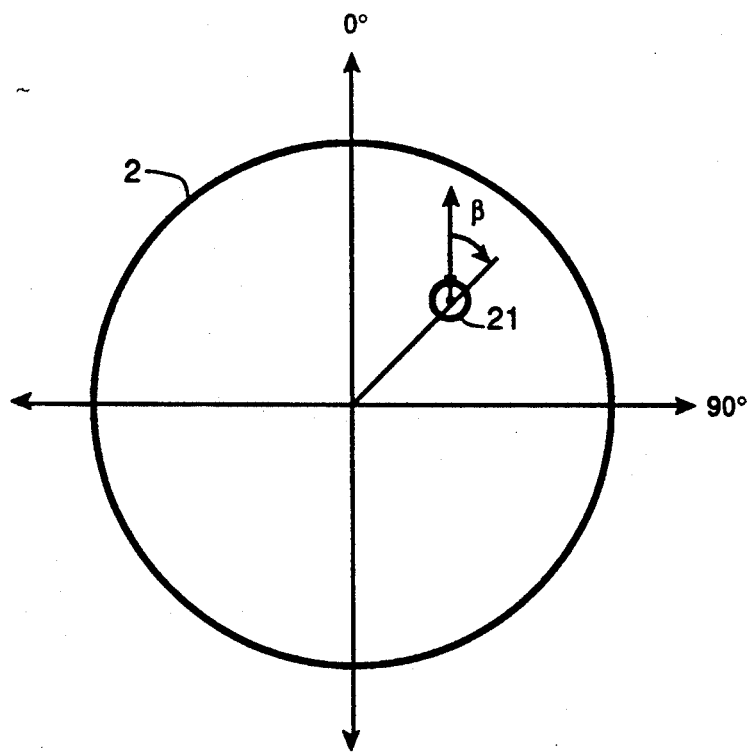
FIG. 4 is a schematic plan view showing the angular orientation of the high side of the incore housing weld.
Figure 4B:
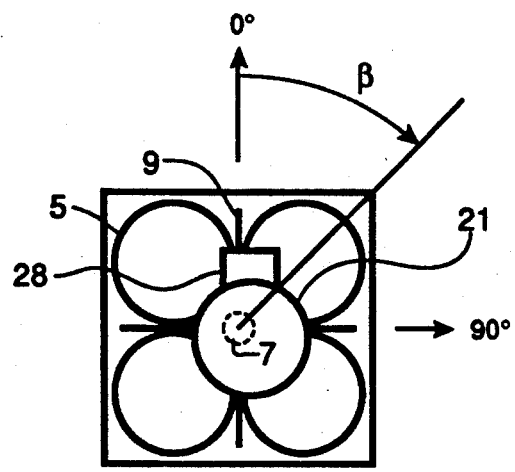

The method of determining the direction of the high side of the housing welds, is shown in FIG. 4. Pressure vessel 2 is assigned a permanent coordinate system with a central origin. Scanning tool 21 is mounted on top guide 9 with clamp 28 secured to top guide 9. When the inspection equipment is first lowered into pressure vessel 2 and clamped into place the probe (the straight-on transducer on the probe) faces the 0° reference direction. The angle $\beta$ which the probe must be rotated to face the high side of the weld is determined by the location of scanning tool 21 relative to the origin in the pressure vessel's coordinate system, since the bottom head of pressure vessel 2 is rotationally symmetric. Thus the probe can be oriented to face the high side of the weld by remote-control, given the scanning tool's coordinates, which are the same coordinates as those of the incore housing.

If the initial rotational orientation of the probe is known, then its rotational orientation is known throughout the inspection. Knowing the rotational orientation of the probe gives clues as to the type of indications which might be found, what their size is, and whether they are classified as acceptable or non-acceptable.

Figure 5:
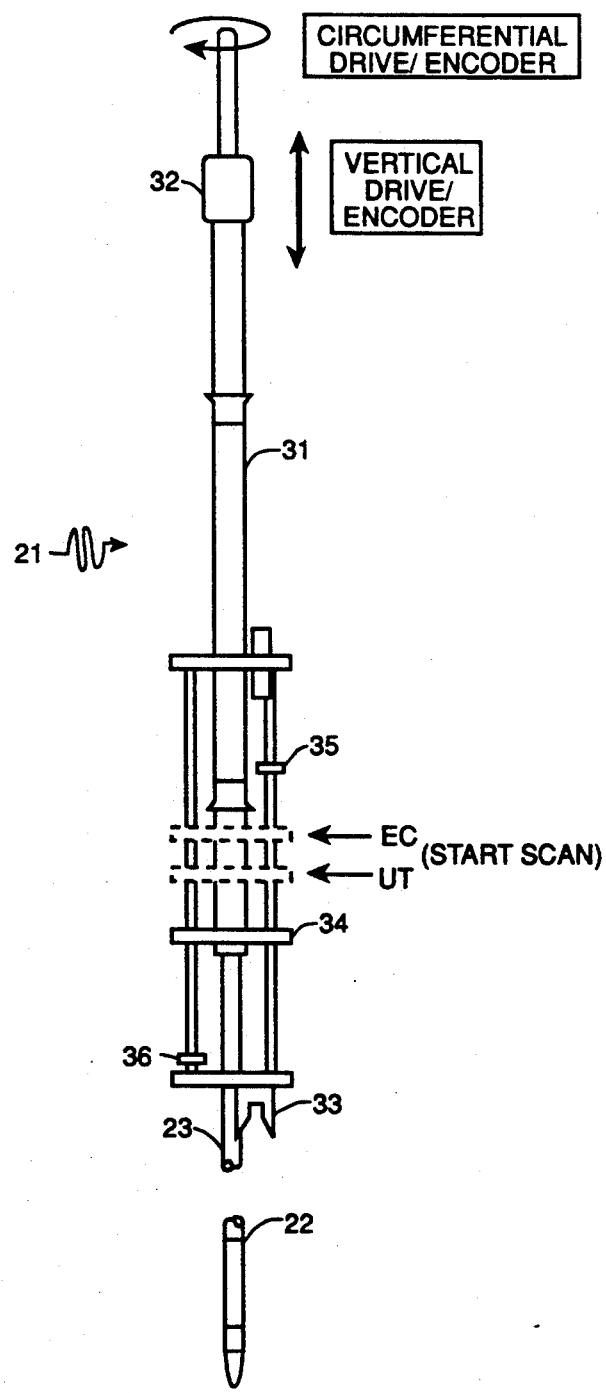
FIG. 5 is a schematic view of the scanning tool.

The basic mechanical components of scanning tool 21 are shown in FIG. 5. Scanning tool 21 comprises a fixture with two DC motors with positioning encoders attached. The DC motors drive the probe in the circumferential and verical directions with encoders providing the positioning data. The mechanical portion of the tool is housed in a cylindrical can which is locked in position on the pressure vessel top guide by a mechanical clamping device.

Probe tube 23 fits through shaft 31, and is clamped thereto with clamp 32 after the length and angular orientation of probe tube 23 is set so probe 22 will initially face the high side of the weld after a rotation through an angle $\beta$, as discussed in connection with FIG. 4. The length of the lower extension of probe tube 23 is set by sliding it vertically through shaft 31 until probe 22 will be at weld level. The rotational orientation is set by aligning scribe marks on probe tube 23 and shaft 31, so the probe will point in the same direction as the mechanical clamping device that fastens scanning tool 21 to the pressure vessel top guide. Brackets 33 also hold scanning tool 21 in place on the top guide. Once in place the circumferential drive rotates shaft 31, probe tube 23, and probe 22 clockwise through the angle $\beta$ to put probe 22 in its initial position before weld inspection.

Once probe 22 is in its initial position the weld and housing tube inspection is performed automatically. Probe 22 is driven with vertical and circumferential drive motors in such a way as to inspect the housing weld and housing tube from at least 40 mm above the weld to at least 40 mm below the weld. In practice, this distance is about 2 inches. The eddy current and ultrasonic inspections are done independently. Probe 22 moves vertically from above the weld to below the weld, then rotates 5°, and moves upwards to above the weld, then rotates 5°. This repeats until it has rotated 360°. The two drive motors each have encoders to control them, based on the position of the probe.

Vertical movement of probe 22 coincides with the movement of travel plate 34, since they are connected via probe tube 23 and shaft 31. Stops 35 and 36 are the upper and lower limits of motion for the travel plate.

The START SCAN position of travel plate 34 before the respective eddy current (EC) and ultrasonic (UT) inspections is different; on probe 22 the eddy current coils are located about 2.7 inches below the ultrasonic transducers. To inspect the same region above the weld, travel plate 34, and hence probe 22, must be raised 2.7 inches higher for the eddy current inspection than for the ultrasonic inspection. The vertical drive moves travel plate 34 down until the eddy current coils are about two inches below the weld for the eddy current inspection, and unitl the uppermost transducer (the straight-on transducer) is about two inches below the weld for the ultrasonic inspection.

Before the automatic scan the initial position of the straight-on transducer is such that it faces the high side of the weld, as mentioned above. More specifically, it faces the top of the high side of the weld. In this way the probe is raised the same amount to inspect the required region above each weld. The amount the probe is lowered is then varied to inspect the required region below the weld. Welds higher up on the bottom head of the pressure vessel are at a greater angle, so the amount the probe is lowered is correspondingly greater.

Figure 6:
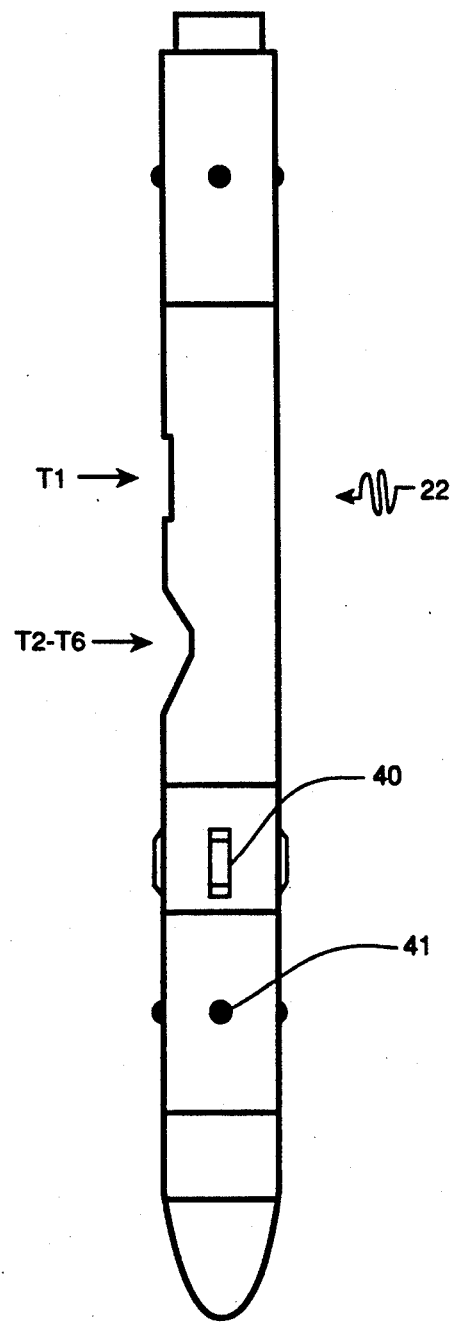
FIG. 6 is a schematic view of the probe.

Probe 22 has six piezo-electric transducers (T1–T6), arranged as shown in FIG. 6. All are turned on during the ultrasonic scan. Transducers T2–T6 are all simultaneously focused so as to interrogate both of the weld fusion zones. They are focused at the same point at the interface between the incore housing and the weld. This permits examination of the entire weld region including the interface between the weld and the bottom head of the reactor. Transducer T1 is focused at the interface between the incore housing and the weld, but above the others.

An arbitrary indication (flaw) shows up if it reflects a portion of the beam back to the transducer that sent it, with the greatest reflection coming back if the indication is perpendicular to the direction of the beam. The transducers are pulsed sequentially, with each pulse followed by a time interval for reception. The elapsed time until reception reveals the location of an indication since the speed of sound in the various materials the beam travels through is known. The magnitude of a reception reveals the size of an indication, due to prior instrument calibration. All examination data is stored by computer techniques, and can be presented graphically with a hard copy printer.

Space considerations cause straight-on transducer T1 to be located about 2 inches above transducers T2–T6. Transducer T1 is aligned with the top of the high side of the weld in question after the scanning tool is clamped to the top guide, as discussed above. Thus, to position transducers T2–T6 about two inches above the top of the high side of a weld, the vertical drive raises the travel plate 4 inches to the UT START SCAN position. The vertical drive then lowers the travel plate until T1 is about 2 inches below the bottom of the weld. (At this point the other five transducers T2–T6 are 4 inches below the weld, which results in additional data in the interval from 2–4 inches below the weld. When T2–T6 are 2 inches above the weld T1 is 4 inches above the weld, which also results in additional data for the region 2–4 inches above the weld.) The probe rotates 5°, then the travel plate returns to the UT START SCAN position, the probe rotates another 5°, and repeats the vertical sweep. This continues until probe 22 has rotated 360° to complete the ultrasonic inspection.

Transducer T1 is a longitudinal tranducer with a frequency of 2.25 MHz. T1 looks straight-on, i.e. perpendicular to probe 22 in a horizontal direction, and is aligned with the top of the high side of the weld before the scan. Its purpose is to provide indication, thickness, and depth information, and to provide information as to the condition of the weld, e.g. cracking, lack of fusion, inclusions, porosity, etc.

There are four 45° shear wave transducers with a frequency of 5.0 MHz. Transducers T2 and T3 look right and left, while transducers T4 and T5 look up and down. Transducers T2 and T3 examine the incore housing and weld circumferentially to detect indications oriented in the axial direction. T4 and T5 examine the volume of material in the axial direction to detect circumferentially oriented indications in the housing and weld. The downward-looking transducer is also used to examine pressure vessel material below the normal plane of coverage.

Transducer T6 is a 60 degree refracted longitudinal wave transducer with a frequency of 2.25 MHz. T6 looks down, and is used to ascertain the condition of the weld build-up area which is present in some incore housing weld designs. In these designs a build-up of weld material is applied to the pressure vessel in such a manner that all the incore housing weld attachments are horizontal.

The eddy current assembly on probe 22 has four coils 40, as shown in FIG. 6. The coils are positioned 90° apart around the lower end of the probe. Two of the four coils are of the absolute type with one coil, and the other two are of the differential type that use two coils for reference and stabilization purposes. The absolute coils are used to provide the required depth of penetration, which is near surface. The differential coils are used to minimize the effect of conductivity and magnetic permeability variations in the heat-affected zone surrounding the weld.

The eddy current assembly is used to examine the inner surface and near surface of the housing for defects. Eddy current coils 40 induce a current in the surface of a conductor, i.e. metal. Variations in the surface of the conductor cause changes in the surface impedance. The changes in impedance have characteristic patterns corresponding to dents, corrosion, or any other flaw with an associated impedence pattern. All examination data is retained digitally on magnetic tape, and can be presented graphically on computer screen and/or be presented in hard copy form with a printer.

The EC START SCAN position of the scanning tool's travel plate is higher for eddy current coils 40 than for the transducers because of their lower position on probe 22, but since coils 40 are at the same level the vertical drive moves them from 2 inches above to 2 inches below the weld without taking into account a coil that is not on the same level. (The vertical sweep is longer for the ultrasonic inspection because transducer T1 is above the others, as previously described.) The eddy current inspection is otherwise identical to the ultrasonic inspection, i.e. vertical sweeps are made in 5° increments until probe 22 has rotated 360°.

Examination of the inner surface and near surface of a housing tube may be done with only one eddy current coil since both the absolute and differential coils provide adequate sensitivity. All four coils are placed into service, however, in case a mechanical problem diminishes the performance of a primary coil. The absolute coils are 0.25 inches in diameter, and the differential coils are 0.125 inches in diameter. Both types operate at nominal frequencies of 100 KHz, but they may be individually driven at other frequencies to provide additional information for analysis. Each coil is spring loaded to maintain contact with the inner surface of the housing tube in order to minimize the effect of lift-off. Spring-loaded balls 41 roll along the inner surface of the incore housing, and help protect eddy current coils 40 from physical damage.

FIGS. 7–12 show the paths of the six transducer beams as they traverse an incore housing weld. In general, indications that present cross-section to the ultrasonic beams will send a reflection back to the probe and be detected.

Figure 7:
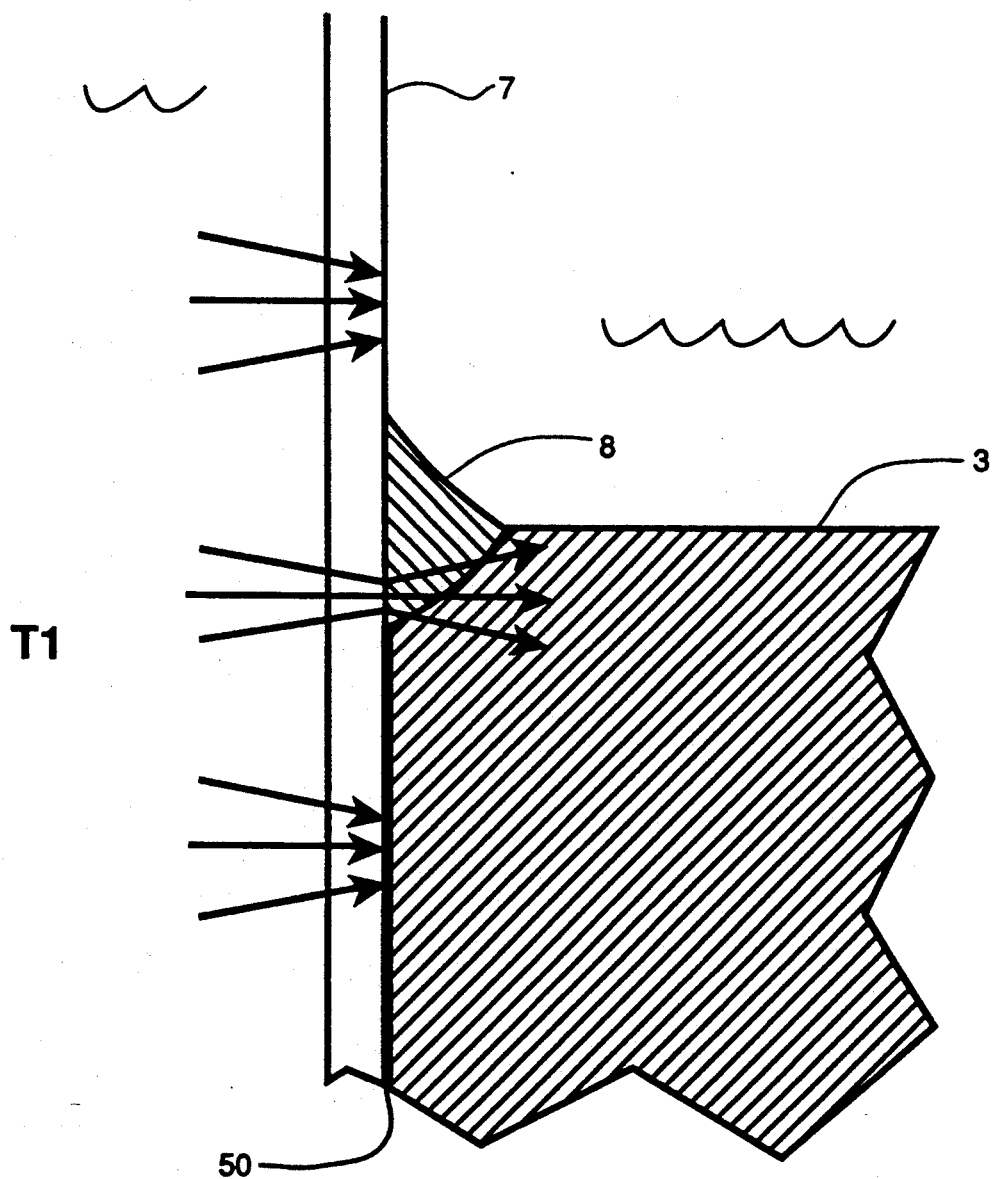
FIG. 7 is a schematic cross-sectional view of the straight ultrasonic transducer path as it crosses the incore housing weld.

FIG. 7 shows the path the beam from transducer T1 follows as the probe passes weld 8 going either up or down. Above weld 8, the beam reflects at the interface between the wall of housing tube 7 and the water inside the pressure vessel. Below weld 8, the beam reflects at the interface between the wall of housing tube 7 and air gap 50, which is present in the region below weld 8 between the wall of housing tube 7 and bottom head 3 of the pressure vessel. When T1 is level with weld 8, the ultrasonic beam diverges at the interface of the wall of housing tube 7 and weld 8, and it passes into bottom head 3 of the pressure vessel, or is reflected at the interface between weld 8 and the water inside the pressure vessel. Arbitrary indications that cause a sufficient reflection back to the probe as it traverses weld 8 will be detected.

Figure 8:
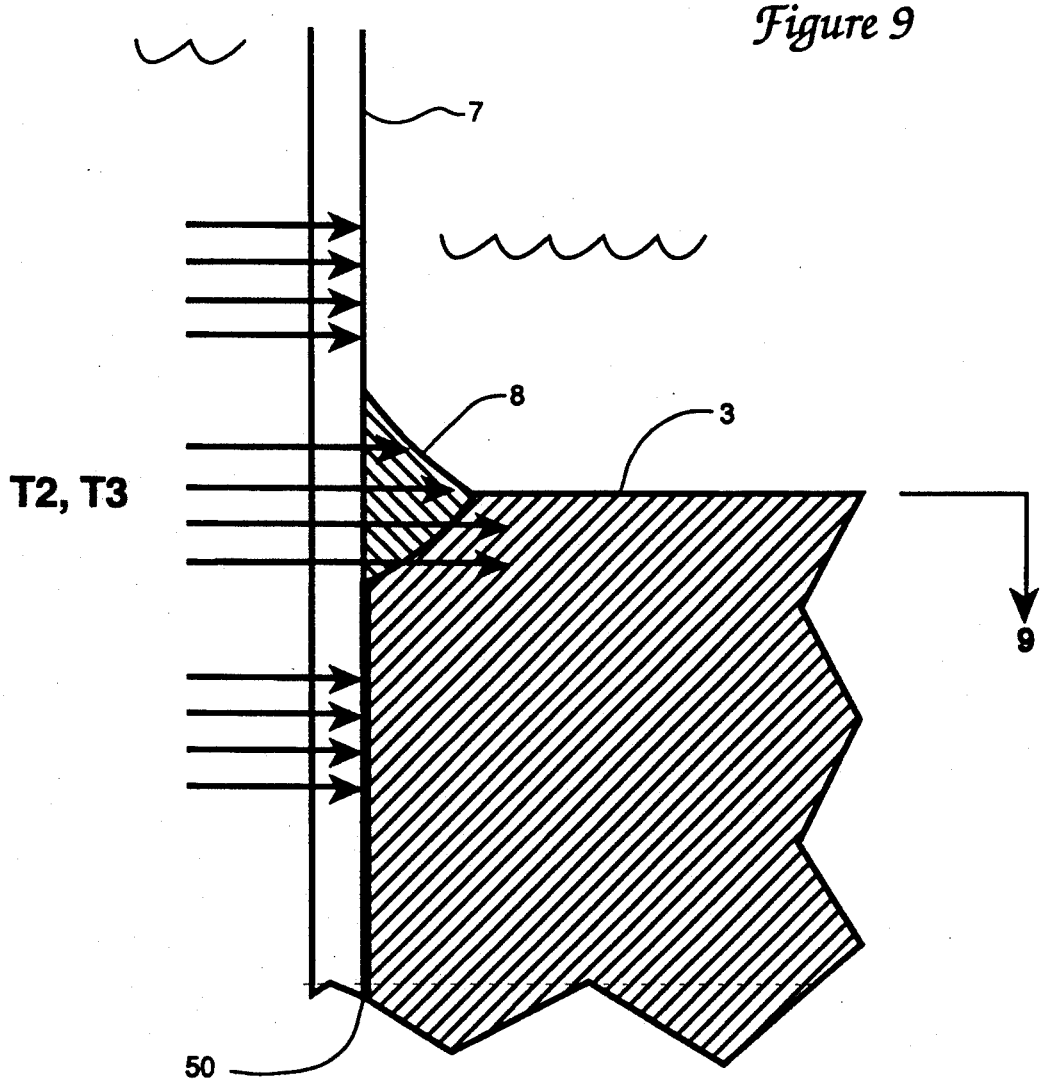
FIG. 8 is a schematic cross-sectional view of the circumferential ultrasonic transducer paths as they cross the incore housing weld.

FIG. 8 shows the paths the beams from transducers T2 and T3 follow as the probe passes weld 8 going either up or down. Above weld 8, the beams reflect at the interface between the wall of housing tube 7 and the water inside the pressure vessel. Below weld 8, the beam reflects at the interface between the wall of housing tube 7 and air gap 50 between housing tube 7 and bottom head 3 of pressure vessel 2. When T2 and T3 are level with weld 8, the ultrasonic beams pass through the interface of the wall of housing tube 7 and weld 8, and go into bottom head 3 of pressure vessel 2, or are reflected at the interface between weld 8 and the water inside the pressure vessel. T2 and T3 are specifically intended to find indications that are axially oriented (lie in the direction of housing tube 7).

Figure 9:
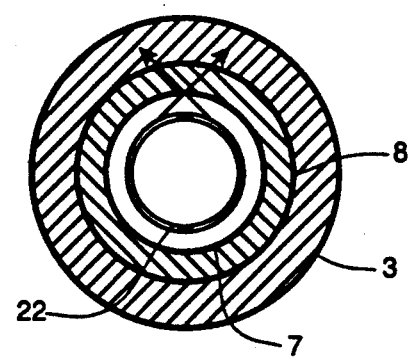
FIG. 9 is a schematic plan view of the circumferential ultrasonic transducer paths as they cross the incore housing weld.

FIG. 9 shows a plan view of the ultrasonic beam paths from transducers T2 and T3 at a single location when they are at weld 8 level. Each beam is oriented 45° in the circumferential direction from T1's beam. Probe 22 essentially fills housing tube 7, and the beams pass through housing tube 7, into weld 8 and bottom head 3 of the pressure vessel. Axial indications are "double checked" from both the clockwise and counter-clockwise directions.

Figure 10:
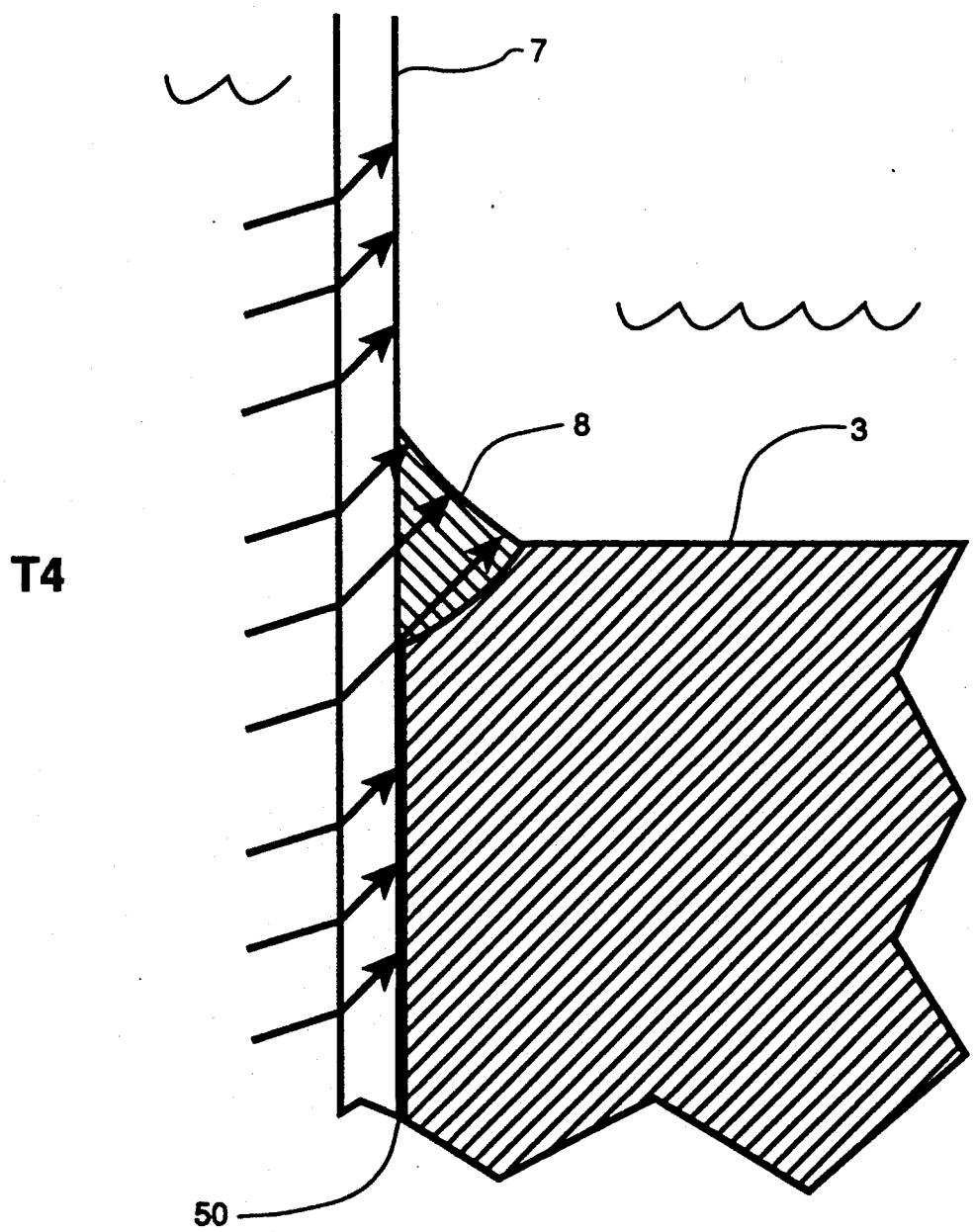
FIG. 10 is a schematic cross-sectional view of the up-looking ultrasonic transducer path crossing the incore housing weld.

FIG. 10 shows the path the beam from transducer T4 follows as the probe passes weld 8 going either up or down. Above weld 8, the beam reflects at the interface between the wall of housing tube 7 and the water inside the pressure vessel. Below weld 8, the beam reflects at the interface between the wall of housing tube 7 and air gap 50, between housing tube 7 and bottom head 3 of the pressure vessel. When T4 is level with weld 8, the ultrasonic beam passes into weld 8 until it is reflected at the interface between weld 8 and the water inside the pressure vessel. T4 is specifically intended to find indications that are circumferentially oriented (tend to lie in a horizontal plane in a direction perpendicular to housing tube 7).

Figure 11:
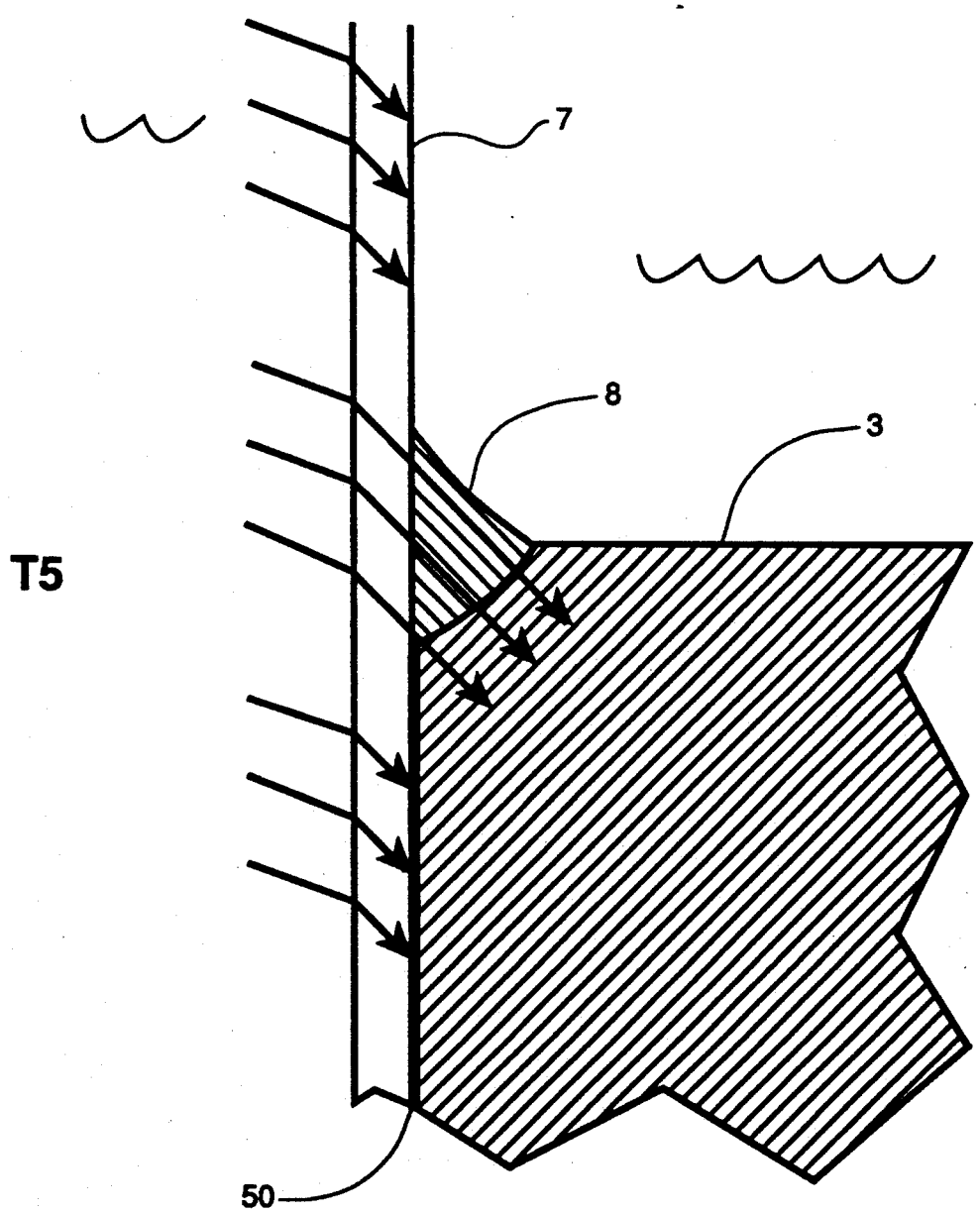
FIG. 11 is a schematic cross-sectional view of the down-looking ultrasonic transducer path crossing the incore housing weld.

FIG. 11 shows the path the beam from transducer T5 follows as the probe passes weld 8 going either up or down. Above weld 8, the beam reflects at the interface between the wall of housing tube 7 and the water inside the pressure vessel. Below weld 8, the beam reflects at the interface between the wall of housing tube 7 and air gap 50, between housing tube 7 and bottom head 3 of the pressure vessel. When T5 is level with weld 8, the ultrasonic beam passes into weld 8 and down into bottom head 3 of the pressure vessel below the normal plane of coverage. T5 is also specifically intended to find indications that are circumferentially oriented. Also, circumferential indications that might tend to be slightly oriented upwards in the direction of the T4 beam will form a greater angle with the T5 beam, and circumferential indications that might be oriented downwards in the T5 direction will form more of an angle with the T4 beam, so circumferential indications are also "double checked" as the probe traverses the weld.

Figure 12:
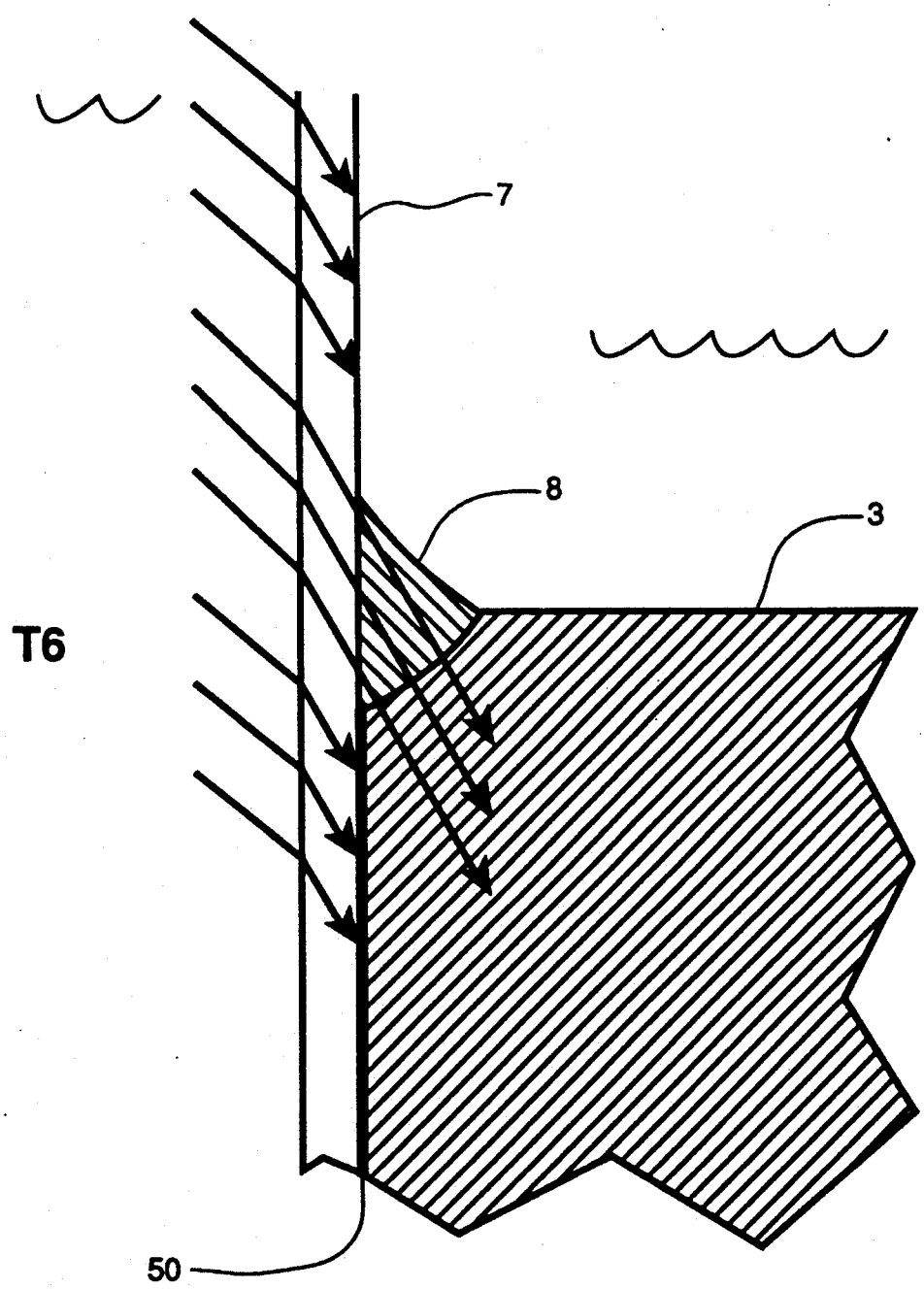
FIG. 12 is a schematic cross-sectional view of the down-looking 60° ultrasonic transducer path as it crosses the incore housing weld.

FIG. 12 shows the path the beam from transducer T6 follows as the probe passes weld 8 going either up or down. Above weld 8, the beam reflects at the interface between the wall of housing tube 7 and the water inside the pressure vessel. Below weld 8, the beam reflects at the interface between the wall of housing tube 7 and air gap 50, between housing tube 7 and bottom head 3 of the pressure vessel. When T6 is level with weld 8, the ultrasonic beam passes into weld 8 and down into bottom head 3 of the pressure vessel below the normal plane of coverage, and closer to housing tube 7 than the T5 beam. Indications that are circumferentially oriented in weld build-up regions, which are employed in some reactor housing attachment welds to make them level, will cause reflections back to the probe as the T6 beam traverses the weld.

Since all the transducers are on during the inspection, an indication will generally show up on more than one transducer read-out. The status of the attachment weld is then known. With the additional information available from the eddy current examination, the status of the entire weld region is determined. It is then possible to decide whether or not repairs are needed.

Because the examination is normally done when the incore instrumentation is tested (and replaced), there is a considerable savings of time and money inspecting the welds from the inside of the incore housing tubes with access from above. This savings is in addition to the greatly increased margin of safety over the prior method of examining the welds from below, in which workers were exposed to high radiation levels. Also, since the entire scanning process is automated, there is a higher standard of precision than the prior method, which was manual.

The invention provides for other embodiments than those described above. For instance, the invention provides for inspection of any circumferential weld about the outside of a tube with access from above, and an overlay suitable for supporting a scanning tool. The weld need not be inside a nuclear reactor pressure vessel. This invention provides for different numbers and types of transducers, depending on the individual circumstances. The transducers need not be focused at the interface of the tube and the weld, but may be focused at other regions of interest. These and other modifications to and variations upon the described embodiments are provided for by the present invention, the scope of which is limited only by the following claims.

We claim:

1. A maintenance procedure for a nuclear reactor, said reactor including a vessel having a top, a bottom, and a wall, said reactor having a core within said vessel, said reactor having an instrumentation guide assembly, said instrumentation guide assembly including an incore housing extending through said bottom, said incore housing being bonded to said vessel by a weld, said instrumentation guide assembly also including a guide tube above, coaxial to and bonded to said incore housing, said guide tube extending at least partially through said core, said reactor having an instrumentation module which can be inserted into said core through said guide tube for monitoring said core, said procedure comprising the steps of:

shutting down said reactor;
  removing said top;
  removing said instrumentation module from said vessel;
  inserting an ultrasonic probe and an attached shaft from above so that said shaft extends through said core and is at least partially immersed in water and through said guide tube and so that said probe extends at least partially into said incore housing;
  mounting a drive unit above said core, said drive unit being coupled to said probe via said shaft;
  operating said drive unit so that it moves said ultrasonic probe vertically and circumferentially in alternation within said incore housing while said ultrasonic probe is activated to detect defects in said weld;

removing said probe from said vessel;

inserting a new instrumentation module into said guide tube;

replacing said top; and restarting the reactor.

2. A method of performing a non-destructive examination of a weld attaching an incore housing to a bottom head of a reactor pressure vessel, wherein said weld at least partially surrounds the external periphery of said incore housing, said method comprising the steps of:

lowering a probe into the interior of said incore housing from above, said probe being mechanically coupled to a scanning drive mechanism via a shaft extending through said core;

clamping said scanning drive mechanism to a top guide at the top of a reactor core of said reactor pressure vessel so as to define a reference circumferential position of said probe within and relative to said reactor pressure vessel, and adjusting the vertical distance between said drive mechanism and said probe so as to define a reference vertical position of said probe within and relative to said reactor pressure vessel; and raster scanning said weld by alternating sweeps in one of the vertical and circumferential dimensions with incremental movements in the other of said dimensions, and while raster scanning pulsing an ultrasound transducer of said probe, said transducer being focussed at points radially beyond incore housing, monitoring reflections received by said ultrasound transducer for indications of defects in said weld, and encoding changes in vertical and circumferential position using encoding means of said drive mechanism so as to track vertical and circumferential position position relative to said reference circumferential and vertical positions so that the absolute position of a defect in said weld within said reactor pressure vessel can be determined.

3. A method as recited in claim 2 further comprising examining the interior surface and near surface thickness of said incore housing using at least one eddy current coil with said probe.

4. A method as recited in claim 3 wherein:

said probe includes multiple transducers and multiple eddy current coils all of said multiple transducers are pulsed during the entire ultrasonic examination;

a plurality of said multiple transducers have the same focal point during the ultrasonic examination to interrogate the same region simultaneously; and all of said said multiple eddy current coils are energized during the entire eddy current examination.

5. A method as recited in claim 4 wherein said incore housing at least partially penetrates said bottom head; and wherein said drive mechanism moves said probe to perform said examination with said multiple eddy current coils and with said multiple transducers so as to cause all of said transducers and all of said eddy current coils to travel from above the highest level of said weld to below the lowest level of said weld during their respective examinations.

6. A method as recited in claim 5 wherein said drive mechanism moves said probe so that all of said transducers and all of said eddy current coils travel from at least 40 millimeters above the highest level of said weld to at least 40 millimeters below the lowest level of said weld.

7. A method as recited in claim 6 wherein said examinations are done with vertical sweeps followed by rotations of about 5° until said probe has rotated at least 360°.

8. A method as recited in claim 7 wherein said probe includes at least one longitudinal wave transducer that faces normal to the surface of said incore housing, said respective examinations beginning with said longitudinal transducer facing so as to traverse past the highest level of said weld in the first vertical sweep of said ultrasonic examination.

9. A system for the non-destructive examination of welds between an incore housing and a bottom head of a reactor pressure vessel of a boiling-water reactor, said system comprising:

a probe with at least one ultrasonic transducer;

a drive mechanism including a vertical drive along with a vertical positioning encoder and a circumferential drive along with a circumferential positioning encoder, said circumferential drive being independent of said vertical drive, clamping means for clamping said drive mechanism to a top guide at the top of the reactor core of said reactor pressure vessel so as to provide a circumferential reference position for said probe, a drive shaft rigidly coupled to said probe and sufficiently long to extend from said top guide to said bottom head, and vertical adjustment means for selecting a reference vertical position of said probe; and electronic means for causing said drive mechanism to alternatively sweep said probe in one of a vertical dimension and a circumferential dimension and step in the other of said dimensions, said electronic means activating and taking data from said ultrasonic transducer, said electronic means coordinating vertical and circumferential movement of said probe with said data collection so the position of any detected defects can be specified.

10. A system as recited in claim 9 wherein said vertical adjustment means includes an extension tube coupling said drive shaft and said probe, said adjustment means also including extension locking means for holding said extension tube in a fixed vertical position, said extension being free to rotate 360° and slide lengthwise through its entire length in said shaft prior to locking.

11. A system as recited in claim 10 wherein said probe includes an eddy current coil.

12. A system as recited in claim 11 wherein said probe includes multiple ultrasonic transducers having the same focal point, said probe also including multiple eddy current coils.

13. A system as recited in claim 12 wherein said multiple eddy current coils include coils of both the absolute and differential type.

14. A system as recited in claim 13 wherein said probe comprises six ultrasonic transducers and four eddy current coils.

15. The system of claim 14 wherein, of said six ultrasonic transducers, three are oriented so their beams are perpendicular to the length of said probe.

16. A system as recited in claim 15 wherein a hoist cable capable of raising and lowering said drive mechanism, said extension, and said probe is attached to said drive mechanism.

* * * * *